(12) United States Patent
Miyamoto et al.

(10) Patent No.: US 6,500,820 B1
(45) Date of Patent: Dec. 31, 2002

(54) PHARMACEUTICAL COMPOSITION FOR NEUROTROPHIC ACTION

(75) Inventors: Masaomi Miyamoto, Takarazuka (JP); Koki Kato, Kobe (JP); Yuji Ishihara, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/673,057
(22) PCT Filed: Apr. 22, 1999
(86) PCT No.: PCT/JP99/02144
§ 371 (c)(1),
(2), (4) Date: Oct. 10, 2000
(87) PCT Pub. No.: WO99/53909
PCT Pub. Date: Oct. 28, 1999

(30) Foreign Application Priority Data

Apr. 23, 1998 (JP) ............................................. 10-113662

(51) Int. Cl.[7] ................................................ A61K 31/55
(52) U.S. Cl. ........................................................ 514/217
(58) Field of Search .......................................... 514/217

(56) References Cited

FOREIGN PATENT DOCUMENTS

| EP | 0487071 A | 5/1992 |
|---|---|---|
| EP | 560235 | 9/1993 |
| JP | 2-169569 | 6/1990 |

OTHER PUBLICATIONS http://www.merck.com/pubs/mmanual/section14/chapter166/166a.htm*

Kato et al., Tak–147, an acetylcholinesterase inhibitor, increases choline acetyltransferase activity in cultured rat septal cholinergic neurons, Jan. 22, 1999, Neuroscience Letters, vol. 260, Issue 1, pp. 5–8.*

(List continued on next page.)

*Primary Examiner*—Frederick Krass
*Assistant Examiner*—Donna Jagoe
(74) *Attorney, Agent, or Firm*—Mark Chao; Elaine M. Ramesh

(57) ABSTRACT

The present invention provides a composition for neurotrophic action which comprises a compound of the formula:

$$Ar-\overset{O}{\overset{\|}{C}}-\underset{R}{\overset{}{C}H}_n-Y$$

wherein

Ar is an optionally condensed phenyl group which may be substituted;

n is an integer of 1 to 10;

R is a hydrogen atom or a hydrocarbon group which may be substituted; and

Y is an amino group which may be substituted or a nitrogen-containing saturated heterocyclic group which may be substituted; or a salt thereof, which compounds are useful for preventing and/or treating (1) neurodegenerative diseases (e.g. senile dementia, Alzheimer's disease, Down's syndrome, Parkinson's disease, Creutzfelt-Jakob disease, amyotrophic lateral sclerosis, diabetic neuropathy, etc.), (2) neuropathy in cerebrovascular diseases (e.g. impairment of cerebral blood flow based on cerebral infarction, cerebral hemorrhage, cerebral sclerosis, etc.), brain trauma, spinal cord injury, cerebritis sequela and cerebral palsy, (4) mental diseases (e.g. depression, panic disorder, schizophrenia, etc.), etc.

4 Claims, 3 Drawing Sheets

OTHER PUBLICATIONS

Yuji Ishihara et al., "Central Cholinergic Agents. 6. Synthesis and Evaluation of 3–[1–(Phenylmethyl)–4–piperidinyl]–1–(2,3,4,5,–tetrahydro–1H–1–benzazepin–8–yl)–1–propanones and Their Analogs as Central Selective Acetylcholinesterase Inhibitors", Journal of Medicinal Chemistry, vol. 37, No.15, pp. 2292–2299 (1994).

J. Fournier et al., "Protective Effects of SR 57746A in Central and Peripheral Models of Neurodegenerative Disorders in Rodents and Primates", Neuroscience vol. 55, No. 3, pp. 629–641 (1993).

Doris Nonner et al., "Neurotrophin Effects on Survival and Expression of Cholinergic Properties in Cultured Rat Septal Neurons under Normal and Stress Conditions", The Journal of Neuroscience, vol. 16(21), pp. 6665–6675 (1996).

* cited by examiner

PHARMACEUTICAL COMPOSITION FOR NEUROTROPHIC ACTION

This application is the National Stage of International Application No. PCT/JP99/02144, filed on Apr. 22, 1999.

TECHNICAL FIELD

The present invention relates to a pharmaceutical composition for neurotrophic action having an excellent properties.

BACKGROUND ART

Proteins such as nerve growth factor (NGF), ciliary neurotrophic factor, insulin growth factor-I and brain-derived neurotrophic factor (BDNF) are known as neurotrophic factors (NTF). They are related to homeostasis of neurons in vivo and have (1) action of survival and retention of neurons, (2) action of synaptic proplasia, (3) action of protecting against cell death and (4) long term potentiation in the hippocampus. It is known that NGF, BDNF, etc. increase choline acetyltransferase (ChAT) activity and that compounds increasing ChAT activity have protective action on nerve cells and neurotrophic action [The Journal of Neuroscience, Vol.16, No.21, pages 6665–6675, (1996) and Neuroscience, Vol.55, No.3, pages 629–641, (1993)].

Therefore, through the above actions, medicines having neurotrophic like action are useful for preventing and/or treating (1) neurodegenerative diseases (e.g. senile dementia, Alzheimer's disease, Down's syndrome, Parkinson's disease, Creutzfelt-Jakob disease, amyotrophic lateral sclerosis, diabetic neuropathy, etc.), (2) neuropathy in cerebrovascular diseases (e.g. impairment of cerebral blood flow based on cerebral infarction, cerebral hemorrhage, cerebral sclerosis, etc.), brain trauma, spinal cord injury, cerebritis sequela and cerebral palsy, (3) dysmnesia (e.g. senile dementia, amnesia, etc.), (4) mental diseases (e.g. depression, panic disorder, schizophrenia, etc.), etc.

As cyclic amine derivatives activating ChAT, Japanese Patent Unexamined Publication No. 169569/1990(H2) describes a compound of the formula:

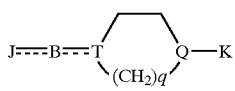

wherein J means (a) a substituted or unsubstituted; ① phenyl, ② pyridyl, ③ pyranyl, ④ quinolyl, ⑤ cyclohexyl, ⑥ quinoxalyl or ⑦ furyl, (b) the following monovalent or divalent group which may be substituted with phenyl; ① indanyl, ② indanonyl, ③ indenyl, ④ indenonyl, ⑤ indanedionyl, ⑥ tetralonyl, ⑦ benzosuberonyl, ⑧ indanonyl and ⑨ a group of the formula:

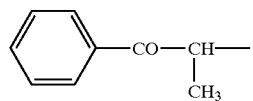

(c) monovalent group induced from cyclic amide compounds, (d) a lower alkyl group, and (e) a group of the formula $R_1$—CH=CH— in which $R_1$ is a hydrogen atom or a lower alkoxycarbonyl group;

B means a group of the formula —CO—$(C(R_2)H)_n$—, etc., wherein n is 0 or an integer of 1 to 10 and $R_2$ means an alkylene group of the formula —$(C(R_2)H)_n$— in which the groups do not have substituents, or means a hydrogen atom or methyl group which have one or more methyl;

T means a nitrogen atom or a carbon atom;

Q means a nitrogen atom, a carbon atom or a group of the formula >N→O;

K means a hydrogen atom, a substituted or unsubstituted phenyl group, an arylalkyl group which may be substituted with phenyl, a cinnamyl group which may be substituted with phenyl, a lower alkyl group, a pyridylmethyl group, a cycloalkylalkyl group, an adamantanemethyl group, furylmethyl group, a cycloalkyl group, a lower alkoxycarbonyl group or an acyl group;

q means an integer of 1 to 3; and

=== means a single bond or a double bond;

or a pharmaceutically acceptable salt thereof.

As cyclic amine derivatives, Japanese Patent Unexamined Publication No. 140149/1993(H5) discloses a fused heterocyclic derivative of the formula:

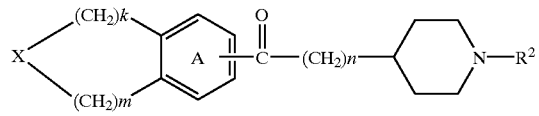

wherein X represents $R^1$—N< ($R^1$ represents a hydrogen atom, a hydrocarbon group which may be substituted or an acyl group which may be substituted), an oxygen atom or a sulfur atom; $R^2$ represents a hydrogen atom or a hydrocarbon group which may be substituted; ring A represents a benzene ring which may be substituted; k represents an integer of 0 to 3; m represents an integer of 1 to 8; and n represents an integer of 1 to 6; or a salt thereof, which inhibits cholinesterase activity.

DISCLOSURE OF THE INVENTION

Figure 1:
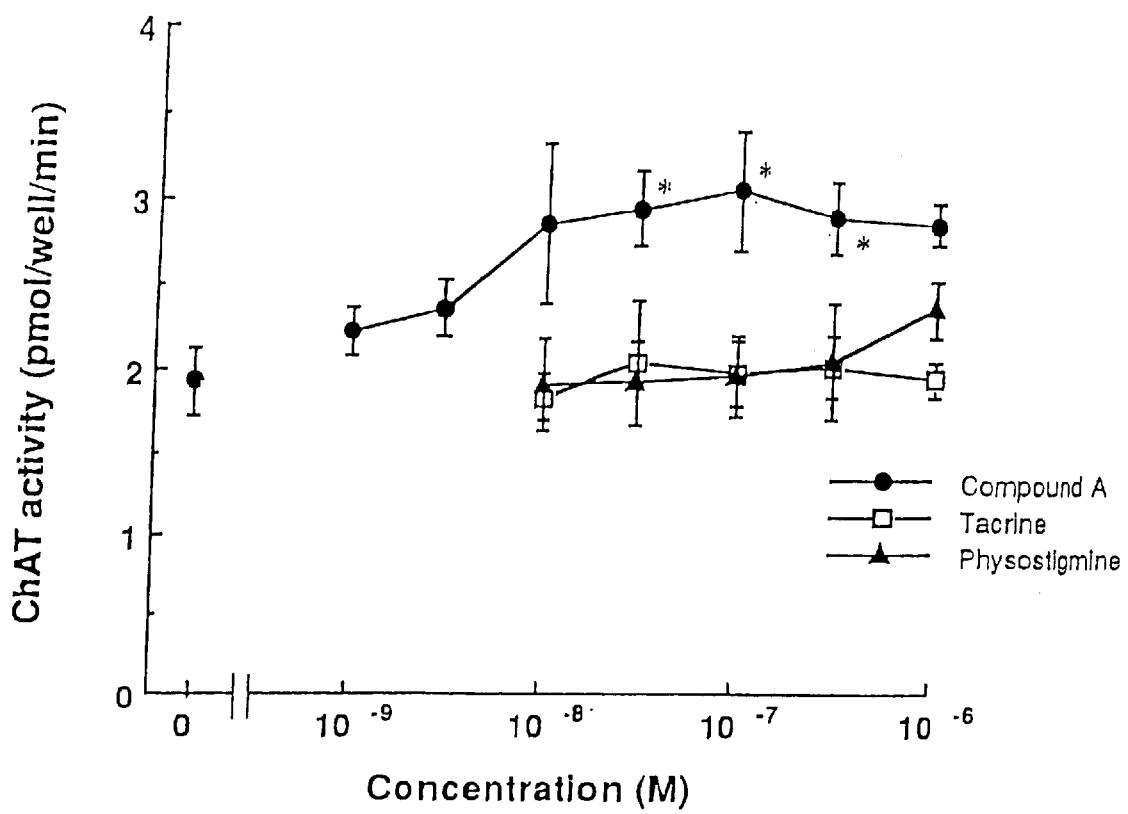
FIG. 1 shows the changes in activation of choline acetyltransferase by the addition of compound A, tacrine or physostigmine in the absence of NGF. In Figure, -●- is compound A, -□- is tacrine and -▲- is physostigmine. Each point represents the mean of 3 separate experiments done in triplicate with the SEM. *$P<0.05$, **$P<0.01$, compared with the control (Dunnett's test).

It has been tried to use NTF for treatment of nerve degenerative disease, neuropathy or dysmnesia, but NTF have faults such as difficulty in oral administration and bad intracranial transfer kinetics, because they are large proteins.

Therefore, it is desired to develop a composition for preventing and/or treating the above diseases which is the low molecular weight and can be administered safety.

The present inventors made intensive studies to solve the above stated problems under the above situation and as a result, they found that a compound of the formula:

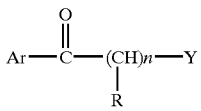

wherein
- Ar is an optionally condensed phenyl group which may be substituted;
- n is an integer of 1 to 10;
- R is a hydrogen atom or a hydrocarbon group which may be substituted; and
- Y is an amino group which may be substituted or a nitrogen-containing saturated heterocyclic group which may be substituted; or a salt thereof (hereinafter abbreviated as compound (I)), have excellent medicinal properties such as unexpected excellent neurotrophic action based on the unique chemical structure, regardless of the substituents.

Namely, the present invention provides
(1) a pharmaceutical composition for neurotrophic action which comprises the compound (I),
    (2) the pharmaceutical composition of the above (1), wherein Ar is a group of the formula:

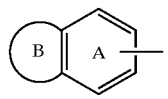

wherein
ring A is a benzene ring which may be substituted;
and ring B is a hetero ring which may be substituted, (3) the pharmaceutical composition of the above (1), wherein Ar is a group of the formula:

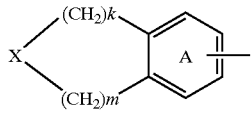

wherein X is an oxygen atom, a sulfur atom or a group of the formula $R^1$—N< in which $R^1$ is a hydrogen atom, a hydrocarbon group which may be substituted or an acyl group, ring A is a benzene ring which may be substituted, k is an integer of Q to 3, and m is an integer of 1 to 8;
n is an integer of 1 to 6;
R is a hydrogen atom; and
Y is a group of the formula

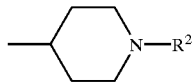

wherein $R^2$ is a hydrogen atom or a hydrocarbon group which may be substituted,
(4) the pharmaceutical composition of the above (1), which comprises 3-[1-(phenylmethyl)-4-piperidinyl]-1-(2,3,4,5-tetrahydro-1H-1-benzazepin-8-yl)-1-propanone fumarate,
(5) the pharmaceutical composition of the above (4), which is for activation of choline acetyltransferase,
(6) the pharmaceutical composition of the above (1), which is for preventing and/or treating Parkinson's disease or amyotrophic lateral sclerosis, etc.

In the above formula, the "substituent" for the "optionally condensed phenyl group which may be substituted" represented by Ar includes, for example, (i) a lower alkyl group which may be halogenated, (ii) a halogen atom (e.g. fluorine, chlorine, bromine, iodine, etc.), (iii) a lower alkylenedioxy group (e.g. a $C_{1-3}$ alkylenedioxy group such as methylenedioxy, ethylenedioxy, etc.), (iv) nitro group, (v) cyano group, (vi) hydroxy group, (vii) a lower alkoxy group which may be halogenated, (viii) a cycloalkyl group (e.g. a $C_{3-6}$ cycloalkyl group such as cyclopropyl, cyclobutyl, cyclopentyl, cyclohexyl, etc.), (ix) a lower alkylthio group which may be halogenated, (x) an amino group, (xi) a mono-lower alkylamino group (e.g. a mono-$C_{1-6}$ alkylamino group such as methylamino, ethylamino, propylamino, etc.), (xii) a di-lower alkylamino group (e.g. a di-$C_{1-6}$ alkylamino group such as dimethylamino, diethylamino, etc.), (xiii) a 5- to 7-membered cyclic amino group which may have 1 to 3 hetero atoms selected from the group consisting of nitrogen atom, oxygen atom and sulfur atom in addition to one nitrogen atom (e.g. pyrrolidino, piperidino, piperazino, morpholino, thiomorpholino, etc.), (xiv) a lower alkylcarbonylamino (e.g. a $C_{1-6}$ alkylcarbonylamino group such as acetylamino, propionylamino, butyrylamino, etc.), (xv) an aminocarbonyloxy group, (xvi) a mono-lower alkylaminocarbonyloxy group (e.g. mono-$C_{1-6}$ alkylaminocarbonyloxy such as methylaminocarbonyloxy, ethylaminocarbonyloxy, etc.), (xvii) a di-lower alkylaminocarbonyloxy group (e.g. a di-$C_{1-6}$ alkylaminocarbonyloxy group such as dimethylaminocarbonyloxy, diethylaminocarbonyloxy, etc.), (xviii) a lower alkylsulfonylamino group (e.g. a $C_{1-6}$ alkylsulfonylamino group such as methylsulfonylamino, ethylsulfonylamino, propylsulfonylamino, etc.), (xix) a lower alkoxycarbonyl group (e.g. a $C_{1-6}$ alkoxy-carbonyl group such as methoxycarbonyl, ethoxycarbonyl, propoxycarbonyl, isobutoxycarbonyl, etc.), (xx) formyl group, (xxi) carboxyl group, (xxii) a lower alkyl carbonyl group (e.g. a $C_{1-6}$ alkyl-carbonyl group such as acetyl, propionyl, butyryl, etc.), (xxiii) a cycloalkylcarbonyl group (a $C_{3-6}$ cycloalkylcarbonyl group such as cyclopropylcarbonyl, cyclobutylcarbonyl, cyclopentylcarbonyl, cyclohexylcarbonyl, etc.), (xxiv) a carbamoyl group, a thiocarbamoyl group, (xxv) a mono-lower alkylcarbamoyl group (e.g. a mono-$C_{1-6}$ alkyl-carbamoyl group such as methylcarbamoyl, ethylcarbamoyl, propylcarbamoyl, butylcarbamoyl, etc.), (xxvi) a di-lower alkyl-carbamoyl group (e.g. a di-$C_{1-6}$ alkyl-carbamoyl group such as diethylcarbamoyl, dibutylcarbamoyl, etc.), (xxvii) a lower alkylsulfonyl group (e.g. a $C_{1-6}$ alkylsulfonyl group such as methylsulfonyl, ethylsulfonyl, propylsulfonyl, etc.), (xxviii) a cycloalkylsulfonyl group (e.g. $C_{3-6}$ cycloalkylsulfonyl such as cyclopentylsulfonyl, cyclohexylsulfonyl, etc.), (xxix) an aryl group (e.g. $C_{6-14}$ aryl group such as phenyl, naphthyl, anthryl, etc.), (xxx) an aralkyl group (e.g. $C_{7-19}$ aralkyl group such as benzyl, phenethyl, diphenylmethyl, triphenylmethyl, naphthylmethyl, diphenylethyl, phenylpropyl, phenylbutyl, phenylpentyl, etc.), (xxxi) an aralkylcarbonyloxy group (e.g. a $C_{7-19}$ aralkyl-carbonyloxy group such as phenylmethylcarbonyloxy, diphenylmethylcarbonyloxy, diphenylethylcarbonyloxy, etc.), (xxxii) an aryloxy group (e.g. a $C_{6-14}$ aryloxy group such as phenoxy, naphthyloxy, etc.), (xxxiii) an aralkylcarbonyl group (e.g. a $C_{7-19}$ aralkyl-carbonyl group such as phenylmethylcarbonyl, phenylethylcarbonyl, diphenylmethylcarbonyl, diphenylethylcarbonyl, etc.), (xxxiv) an aryloxycarbonyl group (e.g. a $C_{6-14}$ aryloxycarbonyl group such as phenoxycarbonyl, etc.), (xxxv) an aralkylcarbamoyl group (e.g. a $C_{7-19}$ aralkyl-carbamoyl group such as phenylmethylcarbamoyl, etc.), (xxxvi) an arylcarbamoyl group (e.g. $C_{6-14}$ aryl-carbamoyl such as phenylcarbamoyl, etc.), (xxxvii) an aralkylcarbamoyl group (e.g. a $C_{7-19}$ aralkyl-carbonylamino group such as phenylmethylcarbonylamino, etc.), (xxxviii) an aralkylamino group (e.g. a $C_{7-19}$ aralkylamino group such as phenylmethylamino, etc.), (xxxix) an aralkylsulfonyl group (e.g. a $C_{7-19}$ aralkylsulfonyl group such as phenylsulfonyl, etc.), (xxxx) an arylsulfonyl group (e.g. a $C_{6-14}$ arylsulfonyl group such as phenylsulfonyl, etc.), (xxxxi) an aralkylsulfinyl group (e.g. a $C_{7-19}$ aralkylsulfinyl group such as benzylsulfinyl, etc.), (xxxxii) an aralkylsulfonylamino group (e.g. a $C_{7-19}$ aralkylsulfonylamino group such as benzylsulfonylamino, etc.) and (xxxxiii) an arylsulfonylamino group (e.g. a $C_{6-14}$ arylsulfonylamino group such as phenylsulfonylamino, etc.). The above aryl group, aralkyl group, aralkylcarbonyloxy group, aryloxy group, aralkylcarbonyl group, aryloxycarbonyl group, aralkylcarbamoyl group, arylcarbamoyl group, aralkylcarbonylamino group, aralkylamino group, aralkylsulfonyl group, arylsulfonyl group, aralkylsulfinyl group, aralkylsulfonylamino group and arylsulfonylamino group, which may have more 1 to 4 substituents selected from groups consisting of, for example, lower alkyl (e.g. $C_{1-6}$ alkyl such as methyl, ethyl, propyl, isopropyl, butyl, sec-butyl, tert-butyl, pentyl, hexyl, etc.), lower alkoxy (e.g. $C_{1-6}$ alkoxy such as methoxy, ethoxy, propoxy, isopropoxy, n-butoxy, isobutoxy, sec-butoxy, tert-butoxy, etc.), halogen (e.g. chlorine, bromine, iodine, etc.), hydroxy, benzyloxy, amino, mono-lower alkylamino (e.g. mono-$C_{1-6}$ alkylamino such as methylamino, ethylamino, propylamino, etc.), di-lower alkylamino (e.g. di-$C_{1-6}$ alkylamino such as dimethylamino, diethylamino, etc.), nitro, lower alkylcarbonyl (e.g. $C_{1-6}$ alkyl-carbonyl such as acetyl, propionyl, butyryl, etc.), and benzoyl.

The above-mentioned "lower alkyl group which may be halogenated" includes, for example, a lower alkyl group (e.g. a $C_{1-6}$ alkyl group such as methyl, ethyl, propyl, isopropyl, butyl, sec-butyl, tert-butyl, pentyl, hexyl, etc.) optionally having 1 to 3 halogen atoms (e.g. chlorine, bromine, iodine, etc.). Specifically, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. are preferred.

The above-mentioned "lower alkoxy group which may be halogenated" includes, for example, a lower alkoxy group (e.g. a $C_{1-6}$ alkoxy group such as methoxy, ethoxy, propoxy, isopropoxy, n-butoxy, isobutoxy, sec-butoxy, tert-butoxy, etc.) optionally having 1 to 3 halogen atoms (e.g. chlorine, bromine, iodine, etc.). Specifically, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. are preferred.

The above-mentioned "lower alkylthio group which may be halogenated" includes, for example, a lower alkylthio group (e.g. a $C_{1-6}$ alkylthio group such as methylthio, ethylthio, propylthio, isopropylthio, butylthio, isobutylthio, sec-butylthio, tert-butylthio, etc.) optionally. having 1 to 3 halogen atoms (e.g. chlorine, bromine, iodine, etc.). Specifically, methylthio, difluoromethylthio, trifluoromethylthio, ethylthio, propylthio, isopropylthio, butylthio, 4,4,4-trifluorobutylthio, isobutylthio, sec-butylthio, tert-butylthio, pentylthio, hexylthio, etc. are preferred.

Example of condensation of the "phenyl group" of the "optionally condensed phenyl group which may be substituted" includes, for example,
(1) condensation to a monocyclic hetero ring which may be substituted,
(2) condensation to a bicyclic hetero ring which may be substituted or to two same or different monocyclic rings (at least one of the two rings is a monocyclic hetero ring), and
(3) condensation to a tricyclic hetero ring which may be substituted.

The group formed by condensation of the "phenyl group" of the "optionally condensed phenyl group which may be substituted" to a monocyclic hetero ring includes, for example, the group of the formula:

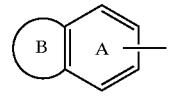

wherein ring A is a benzene ring which may be substituted; and ring B is a hetero ring which may be substituted.

The "substituent" for "benzene ring which may be substituted" represented by ring A may be the same as the "substituent" for the "optionally condensed phenyl group which may be substituted".

The "heterocyclic group" of the "heterocyclic group which may be substituted" represented by ring B includes, for example, a 5- to 14-membered (monocyclic, bicyclic or tricyclic) hetero ring containing 1 to 4 hetero atoms of 1 or 2 species selected from nitrogen atom, sulfur atom and oxygen atom in addition to carbon atoms, preferably, (i) a 5- to 14-membered; more preferably, 5- to 10-membered aromatic hetero ring, (ii) a 5- to 10-membered non-aromatic hetero ring and (iii) a 7- to 10-membered bridged hetero ring, etc.

The above-mentioned "5- to 14-membered, preferably 5- to 10-membered aromatic hetero ring" includes, for example, an aromatic hetero ring such as thiophene, benzothiophene, benzofuran, benzimidazole, benzoxazole, benzothiazole, benzisothiazole, naphtho[2,3-b]thiophene, furan, phenoxadine, pyrrole, imidazole, pyrazole, oxazol, 1,2,4-oxadiazol, 1,3,4-oxadiazol, 1,2,4-thiadiazol, pyridine, pyrazine., pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc., and a ring as formed through condensation of those rings, preferably a monocyclic ring, with one or more, preferably one or two aromatic rings (e.g., benzene ring, etc.), etc.

The above-mentioned "5- to 10-membered non-aromatic hetero ring" includes, for example, pyrrolidine, imidazoline, pyrazolidine, pyrazoline, piperidine, piperazine, morpholine, thiomorpholine, hexamethyleneimine, heptamethyleneimine, tetrahydrofuran, tetrahydrooxazepine, etc.

The above-mentioned "7- to 10-membered bridged hetero ring" includes, for example, quinuclidine, 7-azabicyclo [2.2.1]heptane, etc.

Among others, the 5- to 10-membered non-aromatic hetero ring is preferred.

The "substituent" for the "hetero ring which may be substituted" represented by ring B includes, for example, 1 to 5 groups selected from (i) halogen (e.g. fluorine, chlorine, bromine, iodine, etc.), (ii) nitro, (iii) cyano, (iv) oxo, (v) hydroxy, (vi) lower alkyl (e.g. $C_{1-6}$ alkyl such as methyl, ethyl, propyl, isopropyl, butyl, isobutyl, tert-butyl, sec-butyl, etc.), (vii) lower alkoxy (e.g. $C_{1-6}$ alkoxy such as methoxy, ethoxy, propyloxy, isopropyloxy, butyloxy, etc.), (viii) lower alkylthio (e.g. $C_{1-6}$ alkylthio such as methylthio, ethylthio, propylthio, etc.), (ix) amino, (x) mono-lower alkylamino (e.g. mono-$C_{1-6}$ alkylamino such as methylamino, ethylamino, propylamino, etc.), (xi) di-lower alkylamino (e.g. di-$C_{1-6}$ alkylamino such as dimethylamino, diethylamino, etc.), (xii) 5- to 7-membered cyclic amino (e.g. 5- to 7-membered cyclic amino which may have 1 to 3 hetero atoms selected from nitrogen atom, oxygen atom and sulfur atom in addition to one nitrogen atom such as pyrrolidino, piperidino, piperazino, morpholino, thiomorpholino, etc.), (xiii) lower alkylcarbonylamino (e.g. $C_{1-6}$ alkyl-carbonylamino such as acetylamino, propionylamino, butyrylamino, etc.), (xiv) lower alkylsulfonylamino (e.g. $C_{1-6}$ alkylsulfonylamino such as methylsulfonylamino, ethylsulfonylamino, etc.), (xv) lower alkoxycarbonyl (e.g. $C_{1-6}$ alkoxy-carbonyl such as methoxycarbonyl, ethoxycarbonyl, propoxycarbonyl, etc.), (xvi) carboxyl, (xvii) lower alkylcarbonyl (e.g. $C_{1-6}$ alkyl-carbonyl such as methylcarbonyl, ethylcarbonyl, propylcarbonyl, etc.), (xviii) carbamoyl, thiocarbamoyl, (xix) mono-lower alkylcarbamoyl (e.g. mono-$C_{1-6}$ alkylcarbamoyl such as methylcarbamoyl, ethylcarbamoyl, etc.), (xx) di-lower alkylcarbamoyl (e.g. di-$C_{1-6}$ alkylcarbamoyl such as dimethylcarbamoyl, diethylcarbamoyl, etc.), (xxi) lower alkylsulfonyl (e.g. $C_{1-6}$ alkylsulfonyl such as methylsulfonyl, ethylsulfonyl, propylsulfonyl, etc.).

Among others, oxo and lower alkyl (e.g. $C_{1-6}$ alkyl such as methyl, ethyl, propyl, isopropyl, butyl, isobutyl, tert-butyl, sec-butyl, etc.) are preferred and oxo is commonly used.

When ring B has a nitrogen atom as a ring member, ring B may have a group of the formula >N—$R^1$ wherein $R^1$ is a hydrogen atom, a hydrocarbon group which may be substituted or an acyl group.

The "hydrocarbon group" of the "hydrocarbon group which may be substituted" represented by $R^1$ is the group available upon elimination of one hydrogen atom from a hydrocarbon compound, and specifically includes linear or cyclic hydrocarbon groups such as alkyl group, alkenyl group, alkynyl group, cycloalkyl group, aryl group and aralkyl group. Among others, $C_{1-16}$ hydrocarbon groups which may be formed by linear hydrocarbon groups, cyclic hydrocarbon groups or their combination are preferred.

The above-mentioned hydrocarbon group includes, for example, (1) straight-chain or branched lower alkyl groups (e.g. $C_{1-6}$ alkyl groups such as methyl, ethyl, propyl, isopropyl, butyl, isobutyl, tert-butyl, sec-butyl, pentyl, hexyl, etc.), (2) straight-chain or branched lower alkenyl groups (e.g. $C_{2-6}$ alkenyl groups such as vinyl, allyl, isopropenyl, butenyl, isobutenyl, sec-butenyl, etc.), (3) straight-chain or branched lower alkynyl group (e.g. $C_{2-6}$alkynyl such as propargyl, ethynyl, butynyl, 1-hexynyl, etc.), (4) cycloalkyl groups (e.g. $C_{3-6}$ cycloalkyl groups such as cyclopropyl, cyclobutyl, cyclopentyl, cyclohexyl, etc.), (5) bridged cyclic saturated hydrocarbon group (e.g. bridged cyclic saturated $C_{8-14}$ hydrocarbon group such as bicyclo[3.2.1]oct-2-yl, bicyclo[3.3.1]non-2-yl, adamantan-1-yl, etc.), (6) aryl groups (e.g. $C_{6-14}$ aryl groups such as phenyl, 1-naphthyl, 2-naphthyl, biphenylyl, 2-indenyl, 2-anthryl, etc., preferably, phenyl, etc.), (7) aralkyl groups (e.g. $C_{7-16}$ aralkyl groups such as phenyl-$C_{1-10}$ alkyl (e.g. benzyl, phenylethyl, phenylpropyl, phenylbutyl, phenylpentyl, phenylhexyl, etc.), naphthyl-$C_{1-6}$ alkyl (e.g. α-naphthylmethyl, etc.), diphenyl-$C_{1-3}$ alkyl (e.g. diphenylmethyl, diphenylethyl, etc.), etc.), (8) arylalkenyl groups (e.g. $C_{6-10}$ aryl-$C_{2-6}$ alkenyl groups such as styryl, cinnamyl, 4-phenyl-2-butenyl, 4-phenyl-3-butenyl, etc.), (9) arylalkynyl groups (e.g. $C_{6-10}$ aryl-$C_{2-6}$ alkynyl groups such as phenylethynyl, 3-phenyl-2-propynyl, 3-phenyl-1-propynyl, etc.),

(10) cycloalkyl-alkyl groups (e.g. $C_{3-7}$ cycloalkyl-$C_{1-6}$ alkyl group such as cyclopropylmethyl, cyclobutylmethyl, cyclopentymethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, etc.),

(11) arylaryl groups (e.g. $C_{6-10}$ aryl-$C_{6-10}$ aryl groups such as biphenylyl, etc.), and

(12) aryl-aryl-lower alkyl groups (e.g. $C_{6-10}$ aryl-$C_{6-10}$ aryl-$C_{1-6}$ alkyl groups such as biphenylylmethyl, biphenylylethyl, etc.).

The preferred "hydrocarbon group" of the "hydrocarbon group which may be substituted" represented by R includes, for example, $C_{1-6}$ alkyl, $C_{3-8}$ cycloalkyl, $C_{7-16}$ aralkyl, etc.

The "substituent" of "hydrocarbon group which may be substituted" represented by $R^1$ includes, for example, 1 to 5 (preferably 1 to 3) groups selected from (i) halogen (e.g. fluorine, chlorine, bromine, iodine, etc.), (ii) nitro, (iii) cyano, (iv) oxo, (v) hydroxy, (vi) lower alkyl which may be halogenated (e.g. $C_{1-6}$ alkyl (e.g. methyl, ethyl, propyl, isopropyl, butyl, sec-butyl, tert-butyl, pentyl, hexyl, etc.), optionally having 1 to 3 halogen atoms (e.g. chlorine, bromine, iodine, etc.), specifically, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.), (vii) lower alkoxy which may be halogenated (e.g. $C_{1-6}$ alkoxy such as methoxy, ethoxy, propoxy, isopropoxy, n-butoxy, isobutoxy, sec-butoxy, tert-butoxy, etc.) optionally having 1 to 3 halogen atoms (e.g. chlorine, bromine, iodine, etc.), specifically, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.), (viii) lower alkylthio which may be halogenated (e.g. $C_{1-6}$ alkylthio such as methylthio, ethylthio, propylthio, isopropylthio, butylthio, isobutylthio, sec-butylthio, tert-butylthio, etc.) optionally having 1 to 3 halogen atoms (e.g. chlorine, bromine, iodine, etc.), specifically, methylthio, difluoromethylthio, trifluoromethylthio, ethylthio, propylthio, isopropylthio, butylthio, 4,4,4-trifluorobutylthio, isobutylthio, sec-butylthio, tert-butylthio, pentylthio, hexylthio, etc.), (ix) amino, (x) mono-lower alkylamino (e.g. mono-$C_{1-6}$ alkylamino such as methylamino, ethylamino, propylamino, etc.), (xi) di-lower alkylamino (e.g. di-$C_{1-6}$ alkylamino such as dimethylamino, diethylamino, etc.), (xii) 5- to 7-membered cyclic amino (e.g. 5- to 7-membered cyclic amino which may have 1 to 3 hetero atoms selected from nitrogen, oxygen and sulfur in addition to one nitrogen atom such as pyrrolidino, piperidino, piperazino, morpholino, thiomorpholino, etc.), (xiii) lower alkylcarbonylamino (e.g. $C_{1-6}$ alkylcarbonylamino such as acetylamino, propionylamino, butyrylamino, etc.), (xiv) lower alkylsulfonylamino (e.g. $C_{1-6}$ alkylsulfonylamino such as methylsulfonylamino, ethylsulfonylamino, etc.), (xv) lower alkoxycarbonyl (e.g. $C_{1-6}$ alkoxy-carbonyl such as methoxycarbonyl, ethoxycarbonyl, propoxycarbonyl, etc.), (xvi) carboxyl, (xvii) lower alkylcarbonyl (e.g. $C_{1-6}$ alkyl-carbonyl such as methylcarbonyl, ethylcarbonyl, propylcarbonyl, etc.), (xviii) carbamoyl, thiocarbamoyl, (xix) mono-lower alkylcarbamoyl (e.g. mono-$C_{1-6}$ alkyl-carbamoyl such as methylcarbamoyl, ethylcarbamoyl, etc.), (xx) di-lower alkylcarbamoyl (e.g. di-$C_{1-6}$ alkyl-carbamoyl such as dimethylcarbamoyl, diethylcarbamoyl, etc.), (xxi) lower alkylsulfonyl (e.g. $C_{1-6}$ alkylsulfonyl such as methylsulfonyl, ethylsulfonyl, propylsulfonyl, etc.), (xxii) lower alkoxycarbonyl-lower alkyl (e.g. $C_{1-6}$ alkyl-carbonyl-$C_{1-6}$ alkyl such as methoxycarbonylmethyl, ethoxycarbonylmethyl, tert-butoxycarbonylmethyl, methoxycarbonylmethyl, methoxycarbonylmethyl, methoxycarbonyl(dimethyl)methyl, ethoxycarbonyl(dimethyl)methyl, tert-butoxycarbonyl(dimethyl)methyl, etc.), (xxiii) carboxy-lower alkyl (e.g. carboxy-$C_{1-6}$ alkyl such as carboxymethyl, carboxyethyl, carboxy(dimethyl)methyl, etc.), (xxiv) heterocyclic group which may be substituted, and (xxv) sulfo.

The "heterocyclic group" of the above-mentioned "heterocyclic group which may be substituted" includes, for example, the group available upon elimination of one hydrogen atom from monocyclic or polycyclic hetero ring such as bicyclic hetero ring, tricyclic hetero ring, tetracyclic hetero ring and so on, which contain 1 to 6 hetero atoms selected from nitrogen, oxygen and sulfur in addition to carbon atoms.

Among others, the "heterocyclic group" of the "heterocyclic group which may be substituted" is preferably the group available upon elimination of one hydrogen atom from the monocyclic or bicyclic hetero ring.

The "substituent" for the above-mentioned "heterocyclic group which may be substituted" includes, for example, 1 to 5 groups selected from the above-mentioned "substituent" (i) to (xxiii) and (xxv) of the "hetero ring which may be substituted" represented by ring B.

The "acyl group" represented by $R^1$ includes, for example, formyl, $C_{1-6}$ alkyl-carbonyl (e.g. acetyl, trifluoroacetyl, etc.) which may be halogenated, 5- or 6-membered heterocyclic carbonyl (e.g. pyridylcarbonyl, thienylcarbonyl, furylcarbonyl, etc.), $C_{6-10}$aryl-carbonyl which may be substituted by $C_{1-4}$ alkyl and/or $C_{1-4}$ alkoxy (e.g. benzoyl, methylbenzoyl, methoxybenzoyl, etc.), $C_{6-10}$ arylsulfonyl (e. g. benzenesulfonyl, naphthylsulfonyl, etc.), and 5- or 6-membered heterocyclic sulfonyl (e.g. thienylsulfonyl, etc.). A preferable example of $R^1$ is hydrogen.

A preferable example of the "optionally condensed phenyl group which may be substituted" represented by Ar is the group of the formula:

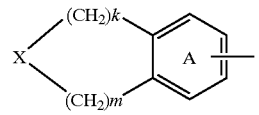

wherein k is an integer of 0 to 3, m is an integer of 1 to 8, n is an integer of 1 to 6, X is an oxygen atom, a sulfur atom or a group of the formula $R^1$—N< in which $R^1$ is as defined above and ring A is as defined above. A more preferable example is a group of the formula:

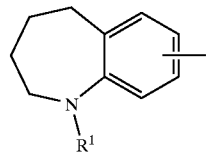

wherein $R^1$ is as defined above. Preferably $R^1$ is hydrogen.

Preferably n is an integer of 1 to 6, more preferably 2 to 6, most preferably 2.

R is a hydrogen atom or an optionally substituted hydrocarbon group, and may be different by a repetition of n. R may combine with Ar or the substituents of Ar.

The "optionally substituted hydrocarbon group" represented by R includes, for example, the above-mentioned optionally substituted hydrocarbon group represented by $R^1$.

A preferable example of R is a hydrogen atom.

The "optionally substituted amino group" represented by Y includes, for example, a group of the formula:

wherein $R^3$ and $R^4$ are a hydrogen atom, an optionally substituted hydrocarbon group or an acyl group.

The "optionally substituted hydrocarbon group" represented by $R^3$ or $R^4$ includes, for example, the above-mentioned "optionally substituted hydrocarbon group" represented by $R^1$. Preferable examples are (1) lower alkyl group (preferably, $C_{1-6}$ alkyl) which may be substituted by 1 to 3 groups selected from halogen, lower alkoxy and hydroxy and (2) aralkyl group (preferably, $C_{7-16}$ aralkyl) which may be substituted by 1 to 3 groups selected from halogen, lower alkoxy and hydroxy.

The "acyl group" represented by $R^3$ or $R^4$ is the above-mentioned "acyl group" represented by $R^1$.

The "nitrogen-containing saturated heterocyclic group" of the "nitrogen-containing saturated heterocyclic group which may be substituted" represented by Y includes, for example, 5- to 9-membered nitrogen-containing saturated heterocyclic groups containing 1 to 3 hetero atoms selected from nitrogen, sulfur and oxygen atoms in addition to carbon atoms and one nitrogen atom. These "nitrogen-containing saturated heterocyclic groups" may have a bond on a nitrogen atom on a carbon atom which is part of the ring. Specifically, the nitrogen-containing saturated heterocyclic group of the formula:

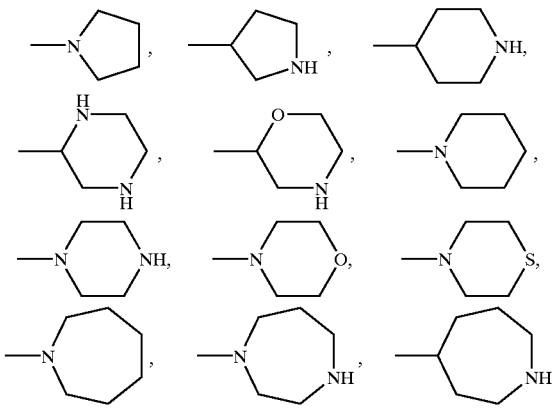

are preferred, and

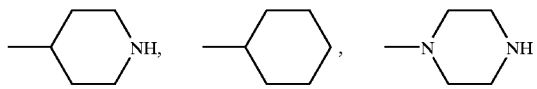

are more preferred.

The "substituent" of the "nitrogen-containing saturated heterocyclic group" includes, for example, 1 to 3 groups of the "optionally substituted hydrocarbon group" represented by $R^1$.

A preferable example of Y is a group of the formula:

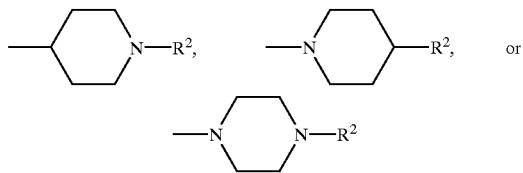

wherein $R^2$ is a hydrogen atom or an optionally substituted hydrocarbon group.

A more preferable example of Y is the group of the formula:

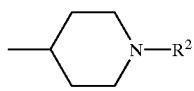

wherein $R^2$ is as defined above.

The "optionally substituted hydrocarbon group" represented by $R^2$ includes, for example, the above-mentioned "optionally substituted hydrocarbon group" represented by $R^1$. A preferable example of $R^2$ is $C_{7-16}$ aralkyl (e.g. phenyl-$C_{1-10}$ alkyl (e.g. benzyl, phenylethyl, phenylpropyl, phenylbutyl, phenylpentyl, phenylhexyl, etc.), naphthyl-$C_{1-6}$ alkyl (e.g. α-naphthylmethyl, etc.), diphenyl-$C_{1-3}$ alkyl (e.g. diphenylmethyl, diphenylethyl, etc.), etc.) which may be substituted, more preferably benzyl.

In the compound (I), Ar is preferably a group of the formula:

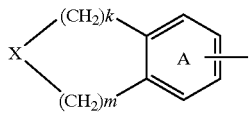

wherein X is an oxygen atom, a sulfur atom or a group of the formula $R^1$—N< in which $R^1$ is a hydrogen atom, a hydrocarbon group which may be substituted or an acyl group, ring A is a benzene ring which may be substituted, k is an integer of 0 to 3, and m is an integer of 1 to 8;

n is an integer of 1 to 6;

R is a hydrogen atom; and

Y is a group of the formula

wherein $R^2$ is a hydrogen atom or a hydrocarbon group which may be substituted, more preferably, 3-[1-(phenylmethyl)-4-piperidynyl]-1(2,3,4,5-tetrahydro-1H-1-benzazepin-8-yl)-1-propanone or a salt thereof.

Salts of compound (I) include, for example, salts with inorganic bases, ammonium salts, salts with organic bases, salts with inorganic acids, salts with organic acids, salts with basic or acidic amino acids, etc. Preferred examples of salts with inorganic bases are alkali metal salts such as sodium salts, potassium salts; alkaline earth metal salts such as calcium salts, magnesium salts, barium salts; aluminum salts, etc. Preferred examples of salts with organic bases are salts with trimethylamine, triethylamine, pyridine, picoline, ethanolamine, diethanolamine, triethanolamine, dicyclohexylamine, N,N'-dibenzylethylenediamine, etc. Preferred examples of salts with inorganic acids are hydrochlorides, hydrobromides, nitrates, sulfates, phosphates, etc. Preferred examples of salts with organic acids are formates, acetates, trifluoroacetates, fumarates, oxalates, tartrates, maleates, citrates, succinates, malates, methanesulfonates, benzenesulfonates, p-toluenesulfonates, etc. Preferred examples of salts with basic amino acids are salts with arginine, lysine, ornithine, etc. Preferred examples of salts with acidic amino acids are aspartates, glutamates, etc.

Among others, pharmaceutically acceptable salts are preferred. For example, for the compound (I) having an acidic functional group in the molecule, mentioned are their inorganic salts such as alkali metal salts (e.g., sodium salts, potassium salts, etc.) and alkaline earth metal salts (e.g., calcium salts, magnesium salts, barium salts, etc.), ammonium salts, etc.; and for the compound (I) having a basic functional group in the molecule, mentioned are their inorganic salts such as hydrobromides, nitrates, sulfates, phosphates, etc. and organic salts such as acetates, maleates, fumarates, succinates, citrates, tartrates, methanesulfonates, p-toluenesulfonates, etc.

Compound (I) may be hydrated or unhydrated.

Compound (I) can be produced in any per se known manner, for example, the methods disclosed in Japanese Patent Unexamined Publication No. 173867/1991(H3), Japanese Patent Unexamined Publication No. 79151/1989 (S64) (EP-A-0296560), Japanese Patent Unexamined Publication No. 140149/1993(H5) (EP-A048071), Japanese Patent Unexamined Publication No. 166676/1994(H6) (EP-A-0560235), Japanese Patent Unexamined Publication No.

206875/1994(H6) (EP-A-0567090), Japanese Patent Unexamined Publication No. 169569/1990(H2) (U.S. Pat No. 4,895,841), Japanese Patent Unexamined Publication No. 206854/1995(H7) (EP-A-0607864) and Japanese Patent Unexamined Publication No. 309835/1995(H7) (EP-A-0655451) or analogous methods thereto.

The compound (I) has an excellent neurotrophic action and activation of neurotrophic factor, etc. Among the compound (I), for example, a compound of the formula:

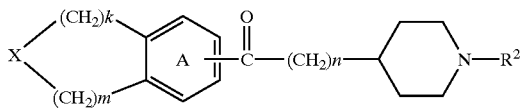

wherein each of the symbols are as defined above, or a salt thereof, have activation of choline acetyltransferase, etc.

Therefore, the compound (I) is useful for preventing and/or treating diseases related to, for example, neurotrophic factor such as (1) neurodegenerative diseases (e.g. senile dementia, Alzheimer's disease, Down's syndrome, Parkinson's disease, Creutzfelt-Jakob disease, amyotrophic lateral sclerosis, diabetic neuropathy, etc.) (2) neuropathy in cerebrovascular diseases (e.g. impairment of cerebral blood flow based on cerebral infarction, cerebral hemorrhage, cerebral sclerosis, etc.), brain trauma, spiral cord injury, cerebritis sequela and cerebral palsy, (3) dysmnesia (e.g. senile dementia, amnesia, etc.), (4) mental diseases (e.g. depression, panic disorder, schizophrenia, etc.), etc.

In preventing and/or treating those disease, the 10 compound (I) can be used in combination with other agents, for example, agents for Parkinson's disease (e.g. Carbidopa+Levodopa, Pergolide, Ropinirole, Cabergoline, Pramipexole, Entacaprone, Lazabemide, etc.), agents for amyotrophic lateral sclerosis (e.g. Riluzzole, Mecasermin, Gabapentin, etc.), agents for depression (e.g. Fluoxetine, Sertraline, Paroxetine, Venlafaxine, Nefazodone, Reboxetine, Imipramine hydrochloride, Duloxetine, etc.), agents for schizophrenia (e.g. Olanzapine, Risperidone, Quetiapine, Iloperidone, etc.), etc.

Furthermore, compound (I) has low toxicity and is used for preventing and/or treating the above-mentioned diseases on mammals (e.g., human, bovine, horse, dog, cat, monkey, mice, rat, preferably human, etc.).

The compound (I) can be formulated into pharmaceutical compositions in any per se known manner, and used either directly as it is, or after having been formulated into pharmaceutical compositions along with pharmaceutically acceptable carriers in any per se known manner, for example, into tablets (including sugar-coated tablets, film-coated tablets), powders, granules, capsules (including soft capsules), liquid preparations, injections, suppositories, sustained release preparations, etc., safely administered orally or parenterally (e.g., locally, rectally, intravenously, etc.).

In the pharmaceutical composition of the present invention, the amount of compound (I) is from about 0.1 to about 100% by weight or so of the total weight of the composition. Though the dose of the composition varies, depending on the subject to which the composition is administered, the administration route employed, the disorder of the subject, the symptom, etc., for example, as a oral composition for treatment of Parkinson's disease, its dose for adults (body weight about 60 kg) for one day may be from about 0.1 to about 200 mg/kg of body weight or so, preferably from about 1 to about 100 mg/kg of body weight or so, more preferably from about 2 to about 5 mg/kg of body weight or so and this may be administered once or, several times a day.

Any ordinary organic and inorganic carrier substances that are generally used in formulating medicines are usable as the pharmaceutical acceptable carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, olive oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

Best Mode for Carrying Out the Invention

The invention will be described in more detail hereinafter, with reference to the following Examples and Experimental Examples, which, however, are to concretely illustrate some embodiments of the invention and are not intended to restrict the scope of the invention. Various changes and modifications can be made within the range that does not deviate from the scope of the invention.

EXAMPLES

Example 1

Film-coated tablet containing 3-[1-(phenylmethyl)-4-piperidinyl]-1-(2,3,4,5-tetrahydro- 1H-1-benzazepin-8-yl)-1-propanone fumarate (hereinafter abbreviated to compound A) Formula:

TABLE 1

| composition | compound weight (mg) |
| --- | --- |
| compound A | 8.0 |
| D-mannitol | 74.0 |
| corn starch | 14.3 |
| hydroxypropylcellulose | 3.0 |
| magnesium stearate | 0.7 |
| total (uncoated-tablet) | 100.0 |
| uncoated-tablet | 100.0 |
| (film component) | |
| hydroxypropyl methylcellulose 2910 | 3.592 |
| titanium dioxide | 0.4 |
| yellow ferric oxide | 0.008 |
| total | 104.0 |

In a fluid-bed granulator (FD-5S, Powrex), compound A (440 g), D-mannitol (4070 g) and corn starch (605 g) were mixed uniformly. The mixture was granulated after spraying with an aqueous solution dissolving hydroxypropylcellulose (HPC-L)(160 g), and was dried in the machine. Thus-obtained granules were milled by using a 1.5 mm φ punching screen in a power mill. To these milled granules (4704 g) were added corn starch (161.7 g) and magnesium stearate (34.3 g) and they were mixed in a tumbler mixer to make granule for tablet. Thus-obtained granules were compressed into tablets by using 6.5 mm φ punch with 100 mg weight in a tableting machine to give uncoated-tablets.

Hydroxypropyl methylcellulose 2910 (TC-5, Shinetsu Chemical Industries) was dissolved and the solution was mixed with an aqueous suspension dispersing titanium dioxide and yellow ferric oxide. In a coating machine (DRC-500), the uncoated-tablets were sprayed with the coating fluid to manufacture about 42000 film-coated tablets each containing 8 mg of the compound A.

Example 2

Film-coated tablet containing the compound A Formula:

TABLE 2

| composition | compound weight (mg) |
| --- | --- |
| compound A | 16.0 |
| D-mannitol | 148.0 |
| corn starch | 28.6 |
| hydroxypropylcellulose | 6.0 |
| magnesium stearate | 1.4 |
| total (uncoated-tablet) | 200.0 |
| uncoated-tablet | 200.0 |
| (film component) | |
| hydroxypropyl methylcellulose 2910 | 7.136 |
| titanium dioxide | 0.8 |
| yellow ferric oxide | 0.064 |
| total | 208.0 |

According to Example 1, the granules were compressed into tablets by using a 8 mm φ punch with 200 mg weight in a tableting machine. Using these uncoated-tablets, about 21000 film-coated tablets each containing 16 mg of the compound A were manufactured.

Experimental Example 1

Methods

This experiment was done by a method reported by Pharmacology of Neurotrophic Factors, Ann. Rev. Pharmacol. Toxicol., Vol.37, pages 239–267, (1997).

Astrocytes were obtained from the new-born Sprague-Dawley (SD) rat hippocampus by trypsin digestion and cultured in a serum-containing medium in a culture flask. The confluent astrocytes were harvested and seeded on 96 well plates at the density of $5 \times 10^4$ cells/well and served as the feeder layer for neurons after halting the overgrowth with 10 μM cytosine arabinoside. Neurons were taken from the septal area of E17 fetal SD rats by trypsin digestion and seeded on the astrocyte feeder layer at the density of $7.5 \times 10^4$ cells/well in a serum-free medium. On the next day, the compound was added to the culture with or without 3 ng/ml recombinant human NGF (rhNGF) and cultured further for 7 days. Then cells were lysed with 5 mM Tris-HCl (pH 7.4)/0.1% Triton X-100 and choline acetyltransferase (ChAT) activity was measured radiometrically by the method of Fonnum.

Results

1) In the condition without rhNGF, compound A (10–1000 nM) apparently increased ChAT activity in the rat septal neurons cultured on the rat hippocampal astrocyte feeder layer in a concentration-dependent manner. However, tacrine and physostigmine which inhibit acetyl cholinesterase activity did not affect ChAT activity (FIG. 1).

Figure 2:
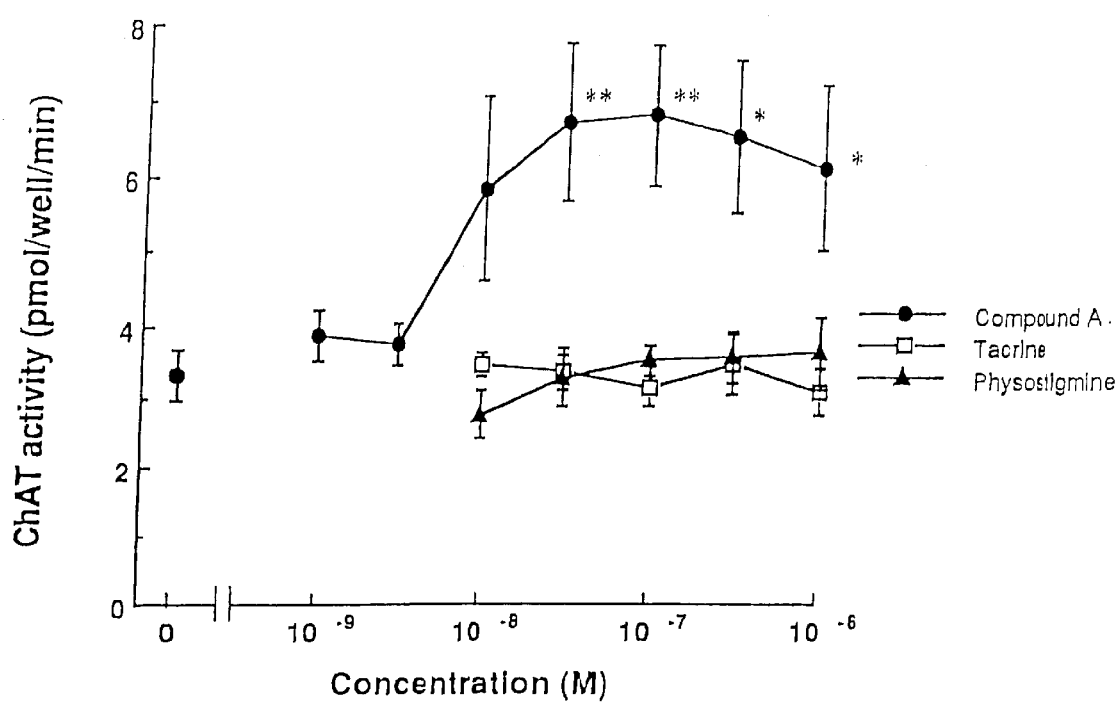
FIG. 2 shows the changes in activation of choline acetyltransferase by the addition of compound A, tacrine or physostigmine in the presence of NGF 3 ng/ml. In Figure, -●- is compound A, -□- is tacrine and -▲- is physostigmine. *$P<0.05$, **$P<0.01$, compared with the control (Dunnett's test).
Figure 3:
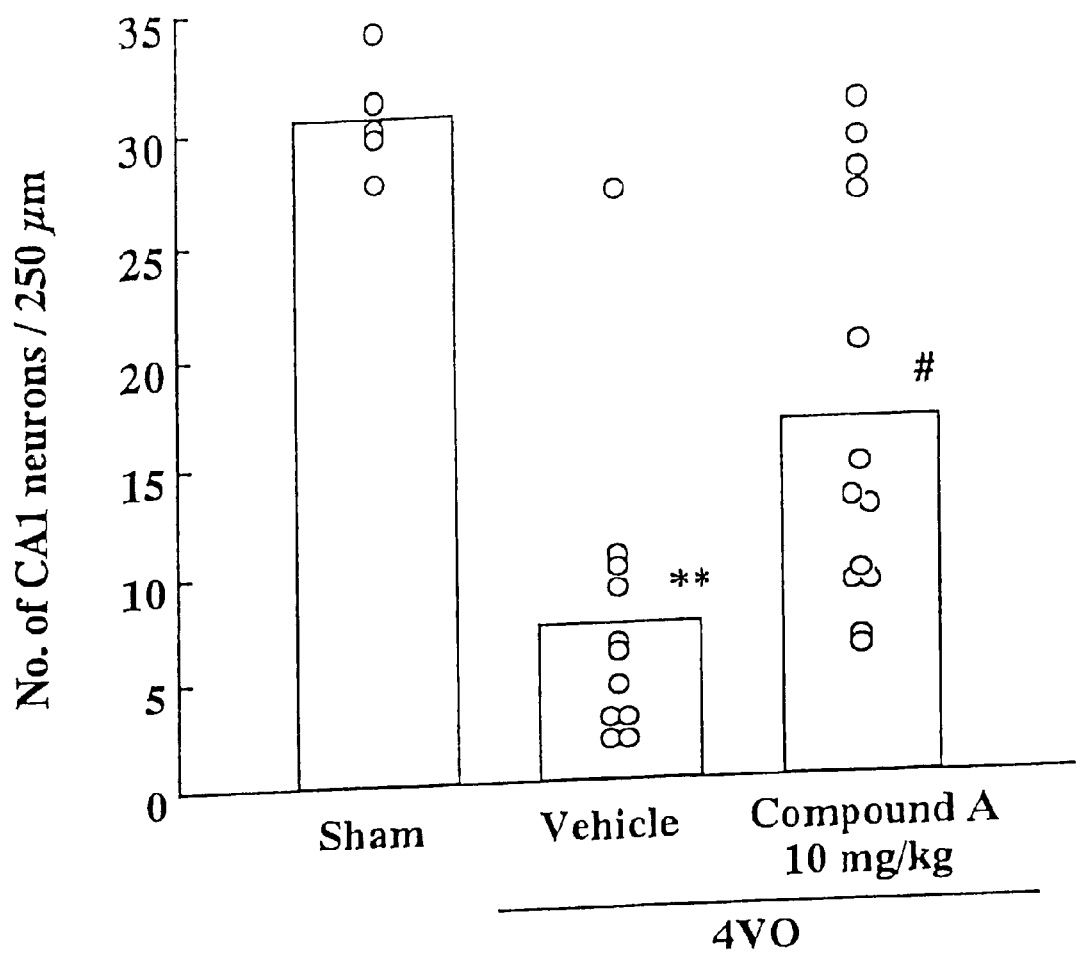
FIG. 3 shows the number of CA1 neurons in the administration of compound A (10 mg/kg) in rats with 4-vessels occlusion(4 VO) for 10 min, sham-operated control and the vehicle-treated 4 VO control. **$P<o.01$, compared with the sham-operated control and #$P<0.05$, compared with the vehicle-treated 4 VO control (Student t-test).

2) Compound A (10–1000 nM) markedly elevated ChAT activity also in the presence of 3 ng/ml rhNGF. Tacrine and physostigmine, did not affect ChAT activity in the presence of rhNGF (FIG. 2).

These results indicate that compound A shows neurotrophic action from the low concentration of 10 nm.

Experimental Example 2

Method

Male Wistar rats (Japan Clea Inc., Tokyo, Japan) aged 9 weeks were used. Rats were subjected to 10-min forebrain ischemia using a method reported by Pulsinelli W. A. and Brierley J. B., Stroke, Vol.10, pages 267–272, (1979). Compound A (10 mg/kg) was orally administered 1 hr before and 4 hr after the ischemic operation, and from the next day, it was administered once daily for 6 days.

Rats were sacrificed 7 days after occlusion for histopathological observation. Under deep pentobarbital anesthesia, rats were perfused transcardially with physiological saline solution. The brains were removed, soaked in FAM (formaline:acetic acid:methanol=1:1:8) solution, and embedded in paraffin. Serial coronal sections (6 μm) were cut at the level of the anterior hippocampus, approximately 3.8–4.3 mm posterior to the bregma and stained with hematoxilin and eosin. The number of living pyramidal cells per 250 μm length of CA1 sector were counted under a light microscope. The average of the right and left neuronal densities were defined as the neuronal density for each rat.

Group differences in the number of CA1 pyramidal cells were analyzed using Student t-tests.

Results

Effects of repeated administration of Compound A on survival of CA1 cells are shown in FIG. 1. The number of CA1 cells of the sham-operated rats was about 30 per 250 μm. Ten-min occlusion induced significant cell loss (−75.9%) in the vehicle-treated 4 VO control (P<0.01). Compound A promoted the survival of CA1 neurons, and the number of pyramidal cells in rats treated with Compound A (10 mg/kg) was significantly greater than that of the vehicle-control($P<0.05$).

These results indicate that compound A protects neurons from ischemia-induced cell death.

INDUSTRIAL APPLICABILITY

The compound (I) is useful for a composition for neurotrophic action and preventing and/or treating diseases related to neurotrophic factor such as (1) neurodegenerative diseases (e.g. senile dementia, Alzheimer's disease, Down's syndrome, Parkinson's disease, Creutzfelt-Jakob disease, amyotrophic lateral sclerosis, diabetic neuropathy, etc.), (2) neuropathy in cerebrovascular diseases (e.g. impairment of cerebral blood flow based on cerebral infarction, cerebral hemorrhage, cerebral sclerosis, etc.), brain trauma, spiral cord injury, cerebritis sequela and cerebral palsy, (3) dysmnesia (e.g. senile dementia, amnesia, etc.), (4) mental diseases (e.g. depression, panic disorder, schizophrenia, etc.), etc.

What is claimed is:

1. A method for activating choline acetyltransferase in a mammal in need thereof comprising administering an effective amount of 3-[1-(phenylmethyl)-4-piperidinyl]-1-(2,3,4,5-tetrahydro-1H-1-benzazepin-8-yl)-1-propanone fumarate to said mammal.

2. A method for activating choline acetyltransferase in a mammal in need thereof comprising administering an effective amount of a compound of the formula:

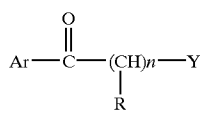

wherein

Ar is an optionally condensed phenyl group which may be substituted;

n is an integer of 1 to 10;

R is a hydrogen atom or a hydrocarbon group which may be substituted; and

Y is an amino group which may be substituted or a nitrogen-containing saturated heterocyclic group which may be substituted;

or a salt thereof to said mammal.

3. The method of claim 2, wherein Ar of said compound is a group of the formula:

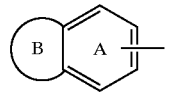

wherein ring A is a benzene ring which may be substituted; and ring B is a hetero ring which may be substituted.

4. The method of claim 2, wherein Ar of said compound is a group of the formula:

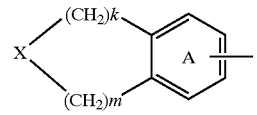

wherein

X is an oxygen atom, a sulfur atom or a group of the formula $R^1$—N< in which $R^1$ is a hydrogen atom, a hydrocarbon group which may be substituted or an acyl group, ring A is a benzene ring which may be substituted, k is an integer of 0 to 3, and m is an integer of 1 to 8;

n is an integer of 1 to 6;

R is a hydrogen atom; and

Y is a group of the formula:

wherein $R^2$ is a hydrogen atom or a hydrocarbon group which may be substituted.

* * * * *